United States Patent
Peyman

(10) Patent No.: US 7,744,860 B2
(45) Date of Patent: Jun. 29, 2010

(54) REDUCED BIOIRRITANT COMPOSITION

(75) Inventor: Gholam A. Peyman, Sun City, AZ (US)

(73) Assignee: Minu LLC, Pittsboro, NC (US)

(*) Notice: Subject to any disclaimer, the term of this patent is extended or adjusted under 35 U.S.C. 154(b) by 425 days.

(21) Appl. No.: 11/254,014

(22) Filed: Oct. 19, 2005

(65) Prior Publication Data

US 2006/0058378 A1 Mar. 16, 2006

Related U.S. Application Data

(60) Continuation-in-part of application No. 11/109,007, filed on Apr. 19, 2005, now Pat. No. 7,223,416, which is a continuation-in-part of application No. 10/803,089, filed on Mar. 18, 2004, now abandoned, and a continuation-in-part of application No. 10/803,090, filed on Mar. 18, 2004, now abandoned, which is a continuation-in-part of application No. 10/200,280, filed on Jul. 23, 2002, now abandoned, which is a division of application No. 09/475,473, filed on Dec. 30, 1999, now Pat. No. 6,436,429, which is a continuation-in-part of application No. 09/340,111, filed on Jun. 28, 1999, now Pat. No. 6,726,922.

(51) Int. Cl.
*A61K 31/74* (2006.01)
(52) U.S. Cl. .................................. 424/78.04
(58) Field of Classification Search .............. 424/427, 424/78.04
See application file for complete search history.

(56) References Cited

U.S. PATENT DOCUMENTS

| | | | |
|---|---|---|---|
| 4,291,017 A | 9/1981 | Beierle et al. | 424/52 |
| 4,291,045 A | 9/1981 | Mackay et al. | 424/270 |
| 4,627,980 A | 12/1986 | Lynch | 424/54 |
| 5,716,625 A | 2/1998 | Hahn et al. | 424/401 |
| 6,436,429 B1 | 8/2002 | Peyman | 424/435 |
| 6,726,922 B1 | 4/2004 | Peyman | 424/427 |

FOREIGN PATENT DOCUMENTS

WO WO 98/43598 * 10/1998

OTHER PUBLICATIONS

Hanashima et al, "reduced Viability of Vascular Endothial Cells by High COncentration of Ascorbic Acid in Vitreous Humor", Cell Biology International, vol. 23, Issue 4, Apr. 1999, pp. 287-298 (abstract only).*
Merriam-Webster Online Dictionary, Definition of "Prophylactic", 2007.*

* cited by examiner

*Primary Examiner*—Carlos A Azpuru
(74) *Attorney, Agent, or Firm*—Thompson Hine LLP

(57) ABSTRACT

A method for reducing irritancy of ascorbic acid administered to a biological surface for anti-angiogenic, anti-oxidant, anti-inflammatory and other effects. It has been discovered that pH neutralized ascorbic acid retains the efficacy of non-pH neutralized ascorbic acid in reducing neovascularization, providing an anti-oxidant effect, etc. but is less irritating and thus enhances patient comfort and compliance. It may be administered into or on the eye, on skin, into a body cavity, etc. either alone or with other agents.

10 Claims, 2 Drawing Sheets
(1 of 2 Drawing Sheet(s) Filed in Color)

REDUCED BIOIRRITANT COMPOSITION

This application is a continuation-in-part of U.S. patent application Ser. No. 11/109,007, filed Apr. 19, 2005, now U.S. Pat. No. 7,223,416 which is a continuation-in-part of U.S. patent application Ser. No. 10/803,089, filed on Mar. 18, 2004, now abandoned and a continuation-in-part of U.S. patent application Ser. No. 10/803,090, filed on Mar. 18, 2004, now abandoned each of which is a continuation-in-part of U.S. patent application Ser. No. 10/200,280, filed on Jul. 23, 2002, now abandoned which is a division of U.S. patent application Ser. No. 09/475,473, filed on Dec. 30,1999, now U.S. Pat. No. 6,436,429, which is a continuation-in-part of U.S. patent application Ser. No. 09/340,111, filed on Jun. 28, 1999, now U.S. Pat. No. 6,726,922, each of which is hereby incorporated by reference in its entirety.

FIELD OF THE INVENTION

The invention is directed to a method for reducing irritancy of an ascorbic acid composition for anti-angiogenic and other effects.

BACKGROUND OF THE INVENTION

Many substances are commonly applied to the skin, mucosal tissue and to other tissues of humans and animals to treat the surface of the skin or tissue. Typical examples of compositions that are applied to the skin include cosmetics, sunscreens and the like. Other compositions often include a pharmaceutical agent such as an antibiotic or bactericide for treating the surface of the tissue.

Topically applied compositions are generally in the form of liquids, creams, pastes, lotions and gels. In many instances, the compositions that are applied topically contain various components which inherently cause irritation and inflammation when applied to the skin or the mucosa. The occurrence and frequency of the irritation can vary depending on the person, the specific components in the composition, and the concentration of components present.

Various compositions for oral use containing acidulants or buffers are generally known. Acidulants are typically included in oral compositions in small amounts as a flavoring agent or flavor enhancer. The compositions usually have a pH that is close to neutral to avoid irritation to the teeth. Various sweeteners are also added to enhance the flavor of the composition. Examples of various oral compositions are disclosed in U.S. Pat. Nos. 4,627,980; 4,291,045; 4,291,017 and 5,912,274.

Common symptoms of irritation from topically applied compositions include itching, stinging, burning, tingling, tightness, redness and swelling. The irritation can be due to the direct effect on the skin or the mucosa of the active ingredient or the carrier, or in response to the immune system directly toward the chemicals or adjuvants alone or in combination with the skin components.

Many ingredients used in topically applied products are known irritants or are potentially irritating, especially for certain people with some allergies or sensitivities. Ingredients which can act as irritants include solvents, fragrances, preservatives, propellants, and pharmaceutical agents. Examples of common topical compositions that can cause irritation include exfolients and skin renewal agents, antiperspirants, antihistamines, anti-inflammatory agents, skin protective agents, insect repellants and sunscreens. Where more than one irritant compound is present, the effects can be additive. In addition, various components can interact with each other to cause irritation which might not occur when used alone.

Efforts have been proposed to attempt to find methods and compositions for reducing or eliminating irritation caused by the topical application of various compositions. For example, one such method attempts to reduce the irritation caused by hydroxy acids and keto-acids in topically applied products by adding a strong alkali base metal such as sodium or potassium hydroxide. The effect of the hydroxide is to raise the pH and to reduce the acidity of the composition. However, this approach has the disadvantage of reducing the effectiveness of the hydroxy acid to penetrate the skin and to reduce the effectiveness of the acid. Other hydroxides and organic amines have also been proposed to adjust the pH of the composition. However, raising the pH using these bases also reduces the effectiveness of the composition.

A further example of methods reducing irritation caused by topically applied compositions is disclosed in U.S. Pat. No. 5,716,625 to Hahn. This patent discloses the use of a strontium metal cation to reduce irritation. It is proposed that the cation interacts with the epidermis nerve cells to prevent or counteract the sensation of irritation by interfering with the irritation inducing components of the skin cells. The strontium cation is proposed to alter the ability of the epidermal cells to depolarize by blocking or interfering with ion channel or pump operation or by altering the transmembranal action potential. It has also been proposed that the strontium cation acts to inhibit or modify the action of skin cell protease or other irritation inducing components.

The human skin and mucosa tissue presents a complicated structural and sensory environment. The skin contains nerves and highly specific sensory cells that are specialized. These cells are developed to differentiate the stimuli leading to specific sensations such as pain. In addition, nerves in the skin are responsive to native or foreign chemicals such as proteases, prostaglandins, complement system molecules, allergens and the like. Agents that are effective in combating one stimulus are often ineffective against another stimulus.

Many pharmaceutical agents when applied topically produce a burning sensation, especially when applied to a cut or sensitive tissue. For example, various eye drops containing a pharmaceutical agent when applied to the eye result in a painful burning of the eye.

Accordingly, there is a continuing need in the industry for providing effective topical agents and a method of reducing or eliminating the pain associated with the topical application of various components.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

SUMMARY OF THE INVENTION

Figure 1A:
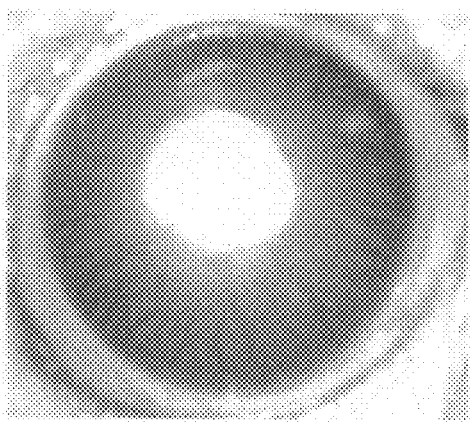
FIGS. 1A-1E are photographs of eyes treated with one embodiment of the invention.
Figure 1B:
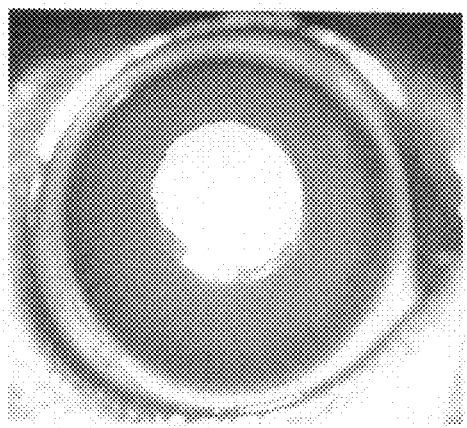
Figure 1C:
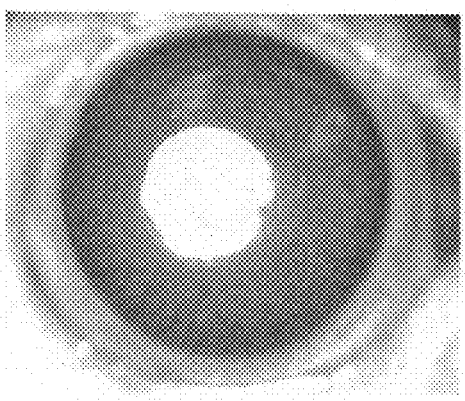
Figure 1D:
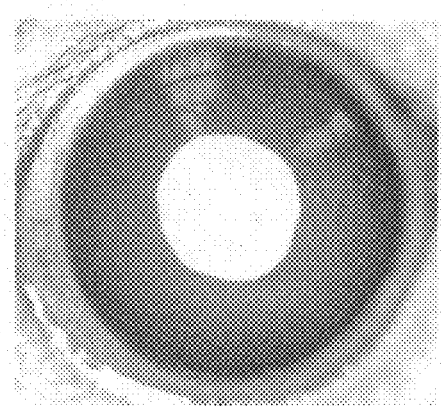

One embodiment is a method of reducing neovascularization using ascorbic acid neutralized to a pH of about 7. The efficacy of ascorbic acid in reducing neovascularization is retained when the normal pH of about 2.5 is adjusted to a pH of about 7, that is, when the ascorbic acid is neutralized. The pH-neutralized ascorbic acid is less irritating to a biological surface to which it is administered. Ascorbic acid at a concentration ranging from about 500 μg/ml up to about 100 mg/ml can be administered to reduce neovascularization, also referred to as an anti-angiogenic effect. It can be administered topically, by injection, by instillation in a body cavity, etc. The method may be used in an individual prone to problems associated with new blood vessel formation such as patients with diabetic retinopathy, age-related macular degeneration, uveitis, ischemic retinopathies, iritis, iritis rubeosis, retinitis of prematurity, cyclitis, sickle cell retinopathy, or to patients undergoing corneal transplant or other ocular surgery, or to patients in which new blood vessel formation is or may be a problem such as individuals exposed to hypoxia, trauma, physical insult, or chemical insult. The composition may also contain other agents such as one or more of a steroid, metalloproteinase inhibitor, non-steroidal anti-inflammatory drug, antibiotic, antiproliferative drug, anti-irritant such as a sweetener, etc.

Another embodiment is a method of reducing neovascularization at a site by applying, either therapeutically or prophylatically, ascorbic acid at a concentration up to about 100 mg/ml in a reduced irritancy composition. The composition may contain a base to neutralize the composition to reduce irritancy, and/or an anti-irritant such as a sweetener to reduce irritancy. The reduced irritancy composition can be better tolerated by a patient when the composition is administered to the eye, or to skin, or to a mucous membrane (e.g., mouth, nose, etc).

Another embodiment is a method of reducing ocular neovascularization by administering up to about 100 mg/ml ascorbic acid adjusted to a pH of about 7 in a biocompatible composition under conditions sufficient to reduce ocular neovascularization.

Another embodiment of the method administers up to about 100 mg/ml ascorbic acid adjusted to a pH of about 7 in a biocompatible composition to a biological surface (e.g., cells, mucous membrane, skin, etc.) under conditions to exert an effect of ascorbic acid (e.g., anti-angiogenic, anti-oxidant, anti-inflammatory, etc.) with reduced bioirritancy. As one example, ascorbic acid at about 50 μg/ml provides an antioxidant effect, so that pH neutralized ascorbic acid at about 50 μg/ml provides an anti-oxidant effect with reduced irritancy to the biological surface to which it is applied. As another example, ascorbic acid from about 250 μg/ml up to about 100 mg/ml provides an anti-angiogenic effect, so that pH neutralized ascorbic acid within this concentration range provides an anti-angiogenic effect with reduced irritancy to the biological surface to which it is applied.

These and other embodiments will be apparent from the following detailed description and examples.

DETAILED DESCRIPTION

One embodiment of the invention discloses the use and formulations of nonsteroidal anti-inflammatory drugs (NSAIDs) for topical application to mucous membranes. In one embodiment, the composition results in containment of viral infections and/or alleviation of symptoms associated with viral infections, allergies, etc. The use of NSAIDs, versus steroids, provides relief without the immunosuppression that is associated with steroid treatment.

While not being limited to a particular theory, the anti-prostaglandin properties of NSAIDs stabilize the cellular endothelial barrier, reducing its breakdown and associated leakage that results in symptoms such as redness, inflammation, itching, irritation, blistering, etc. The anti-prostaglandin properties of NSAIDs can also reduce or prevent viral vesicle formation in skin, and therefore reduce or prevent the virus from breaking and spreading into skin. Viral breakdown of vesicles, using prostaglandins as mediators, allows viral release and attack on the endothelial barrier. Thus, the inventive method of using an anti-prostaglandin may contain and prevent or reduce the spread of virus. Therapy includes any reduction in disease or symptomatic severity, duration, sequalae, and also includes palliative and prophylactic therapy.

The invention is applicable for therapy for diseases that manifest, as one or more symptoms, in a mucous membrane. Some types of disease that affect mucous membranes are classified under the general category of immune mediated subepithelial blistering diseases. These types of diseases include mucous membrane pemphigoid (MMP), bullous pemphigoid (BP), cicatrical pemphigoid (CP), ocular cicatrical pemphigoid (OCP), herpes gestationis, linear IgA disease, and some variants of epidermolysis bullosa. Some of these diseases primarily affect a particular mucous membrane. As one example, MMP almost exclusively affects the oral mucosas, it occasionally may present ocular and skin manifestations. As another example, BP almost exclusively affects the skin, it occasionally may present intraoral manifestations.

The invention is applicable for therapy of allergies, for exacerbations of Herpes simplex virus infections that result in cold sores or fever blisters in mucus membranes including the oral and nasal cavities, for exacerbation of Herpes zoster virus infections that are associated with pain and itching in shingles, for recurrent minor aphthous ulcers or stomatitis (known as mouth ulcers or canker sores) in the oral mucosa, for pathologies such as migraines and asthma, that can be initiated by allergens, and for pruitis associated with allergies and the induced mechanical irritation that results when scratching leads to further itching, infection, irritation, inflammation, etc.

A composition containing one or more NSAID may be administered by topical application. Topical application may be to a mucous membrane, also called mucosa, lining all body passages that communicate with the exterior such as the respiratory, genitourinary, and alimentary tracts, and having cells and associated glands that secrete mucous. Topical application may be to mucous membranes of nose, mouth, eye, eyelid inner surface, etc., or may be to the surface of intact or compromised skin (e.g., applied to a rash, an abrasion, etc.). The composition may be formulated as drops, sprays, ointments, creams, lotions, gels, etc.

The invention includes NSAIDs from known classes, and NSAIDs under development or to be discovered. These include, but are not limited to, derivatives of acetic acid (e.g. diclofenac and ketorolac (Toradol®, Voltaren®, Voltaren-XR®, Cataflam®)); salicylate (e.g., aspirin, Ecotrin®); proprionic acid (e.g., ibuprofen (Advil®, Motrin®, Medipren®, Nuprin®)); acetaminophen (Tylenol®); aniline (e.g., aminophenolacetaminophen; pyrazole (e.g., phenylbutazone); N-arylanthranilic acid (fenamates) (e.g., meclofenamate); indole (e.g., indomethacin (Indocin®, Indocin-SR®)); oxicam (e.g., piroxicam (Feldene®)); pyrrol-pyrrole group (e.g., Acular®); antiplatelet medications; choline magnesium salicylate (Trilisate®), cox-2 inhibitors (meloxicam (Mobic®)); diflunisal (Dolobid®), etodolac (Lodine®); fenoprofen (Nalfon®), flurbiprofen (Ansaid®); ketoprofen (Orudis®, Oruvail®); meclofenamate (Meclomen®); nabumetone (Relafen®); naproxen (Naprosyn®, Naprelan®, Anaprox®, Aleve®); oxaprozin (Daypro®); phenylbutazone (Butazolidine®); salsalate (Disalcid®, Salflex®); tolmetin (Tolectin®); valdecoxib (Bextra®); sulindac (Clinoril®); flurbiprofin sodium (Ocufen®).

One embodiment of the present invention is directed to a process and composition for temporarily suppressing pain and irritation by applying an effective amount of NSAID and/or an anti-irritant to the skin, mucosa, eye or other tissue in an animal, and particularly humans. More particularly, the invention is directed to a process and composition for topically delivering a composition to a specific delivery or target site on a patient where the composition contains an NSAID and/or an anti-irritant in amounts to minimize, reduce, or inhibit irritation to the delivery site.

In some embodiments, the composition contains at least one active component such as an NSAID as a biologically active agent and a suitable vehicle or carrier. It may also contain other components, such as an anti-irritant. The carrier can be a liquid, solid or semi-solid. In various embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. While various embodiments are described herein as liquids, it is to be understood that the compositions of the invention can be produced as solids, such as powders or granules. The solids can be applied directly or dissolved in water or a biocompatible solvent prior to use to form a solution that is substantially neutral or that has been rendered substantially neutral and that can then be applied to the target site.

The composition that is applied to the treatment site can be a liquid or solid depending on the treatment site. For example, the composition can include a solid or semi-solid carrier when the composition is used as a lozenge or tablet for the oral delivery of an active component. In further embodiments the composition can be used as an implant or a suppository. Liquid carriers are desirable in some instances for oral use, such as mouth washes, gargle solutions and the like. Liquid carriers are also desirable for irrigation solutions for irrigating a cut, wound or surgical site, such as during surgical removal of a tumor and irrigating the bladder or vagina. Liquid, and particularly aqueous carriers, are also suitable for topical application to the skin.

The invention is primarily directed to a composition containing one or more NSAIDs, optionally with an anti-irritant agent, in an effective amount for the desired therapeutic treatment (e.g., reduce inflammation, reduce itching, contain virus, inhibit irritation, suppress pain receptors, etc.) to the area being treated topically with the composition.

As previously stated, the present invention applies the composition topically, which includes application to the oral mucosa, which includes the oral cavity, oral epithelium, palate, gingival, and the nasal mucosa. One embodiment of the invention includes a component that reduces or minimizes an unpleasant organoleptic property of the compound. This may include a bitter taste in the mouth or throat, or an unpleasant sensation in the nose. The invention is thus further directed to a process of treating tissue or applying an active agent to an area with little or no irritation. It has been found that various natural and particularly artificial or synthetic non-nutritive sweeteners are able to provide a temporary suppression of pain and irritation to the area being treated when applied topically. In particular, it has been found that compositions using an artificial, non-nutritive sweetener in amounts in excess of the amounts conventionally used for sweetening a food product have an anti-irritant effect. Although not completely understood, and without being bound by a specific theory, it is believed that the natural sweeteners and particularly the synthetic, non-nutritive sweeteners are able to block the pain receptors at the site on the tissue being treated. The non-nutritive artificial sweeteners are particularly effective as anti-irritants when used in amounts in excess of the normal sweetening amount. Patients using the compositions of the invention, when applied topically to skin, mucosa, and other tissue such as the gums, experience a reduction in pain and irritation than would otherwise occur and without numbness or loss of feeling to the treated area.

In embodiments, the anti-irritant is an artificial non-nutritive sweetener included in the composition in an effective amount to suppress or inhibit pain and inhibit irritation caused by topically applying the composition to the skin, mucosa or other tissue. The artificial, non-nutritive sweetener can be a commercially available sweetener such as saccharine and salts thereof, aspartame, cyclamates and salts thereof, acetesulfone K, and mixtures thereof. In embodiments, the non-nutritive sweetener is sodium saccharine obtained commercially as a food sweetener, such as the product available under the trademark Sweet-N-Low®. The commercially available food sweeteners typically include a bulking and dispersing component such as dextrose. The bulking and dispersing components of the commercial sweeteners do not interfere with the anti-irritant effect of the sweetener. Sodium saccharine is generally preferred since it is readily soluble in water and readily available.

In further embodiments, the anti-irritant is a natural sweetener such as a monosaccharide, disaccharide or polysaccharide. Suitable natural monosaccharide sweeteners include glucose and fructose. Other sweeteners include, arabinose, xylose, ribose, mannose, galactose, dextrose, sorbose, sorbitol, mannitol, and mixtures thereof. Suitable disaccharides include sucrose, lactose, maltose and cellobiose. The polysaccharides can include partially hydrolyzed starch, dextrin, stevioside or corn syrup solids. In embodiments of the invention, the natural sweeteners can be used in combination with one or more non-nutritive sweeteners. Examples of suitable sweeteners that can be used in combination include sorbitol, mannitol, xylitol and the like.

In embodiments, the composition of the invention includes a carrier. Water or other pharmaceutically acceptable liquid or solid carriers can be used depending on the intended use of the composition. The carrier can include various co-solvents, dispersing agents or emulsifiers as known in the art. In one embodiment, the carrier is water substantially in the absence of emulsifiers or dispersing agents or cosolvents. Alternatively, the carrier can also contain various thickening or gelling agents to obtain the desired consistency or viscosity. In one embodiment, the composition is a substantially dry composition that is typically in a powder or granular form. The solid can be applied to a target site and dissolved or dispersed in body fluids to form a solution containing the active components for treating the target site. The solid can also be dispersed or dissolved in an amount of water or other solvent to form a solution or dispersion that is then applied to the target site to treat the tissue in the target site.

In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials. Various cosolvents can be used as known in the art to disperse the components and maintain the components in solution or suspension. The vehicles used for compositions for treating mucosa are limited primarily by the toxicity of the vehicle to the tissue. In some embodiments containing an anti-irritant, the anti-irritant is dissolved or dispersed in the liquid carrier in an amount to provide the desired anti-irritant effect. The amount of the anti-irritant will depend on the particular anti-irritant being used, the solubility or dispersibility of the anti-irritant and the active ingredient responsible for the irritation because some active ingredients are more likely to cause irritation. The sensitivity of the intended tissue being treated also determines the amount of the anti-irritant in the composition.

In one embodiment of the invention, the anti-irritant is an artificial sweetener. A suitable sweetener is commercially available sodium saccharine. Sodium saccharine is included in the concentration of about 10% to about 40% by weight based on the total weight of the carrier. The amount of the non-nutritive sweetener can vary depending on the other components of the composition. In one embodiment, the non-nutritive sweetener is used in similar amounts for liquid and solid carriers. Generally, sodium saccharine is included in the concentration of 15% to about 30% by weight based on the total weight of the carrier. Commercially available saccharine products sold as ready-to-use sugar substitutes contain about 60% by weight saccharine, with the remaining amount being made up of dextrose and other bulking, dispersing and anti-caking agents. These commercially available sodium saccharine products are used in concentrations, typically about 25% to 35% by weight, to provide the desired saccharine concentrations in the final composition of the invention. Other artificial non-nutritive sweeteners such as aspartame and cyclamates and salts thereof are used in similar concentrations as saccharine. In further embodiments, the artificial non-nutritive sweetener is included in a concentration to form a saturated solution. The non-nutritive sweeteners are generally used in concentrations of at least 10 wt %, in some embodiments at least 15 wt %, and in some embodiments at least 20 wt % based on the total weight of the composition.

The natural sweeteners, such as sucrose, can be included in the composition in the concentration of about 15% to 30% by weight based on the total weight of the composition. Generally, when the carrier is a liquid, the natural sweetener forms a saturated or near saturated solution. In embodiments, the anti-irritant is an artificial non-nutritive sweetener to avoid the stickiness associated with topical applications of natural sweeteners. In still further embodiments, the composition is an aqueous medium containing a mixture of a natural sweetener, such as sucrose or sorbitol, and an anti-irritant amount of a synthetic sweetener such as sodium saccharine.

Whether or not an anti-irritant is present, the composition contains at least one NSAID in an amount to provide effective treatment of the patient in need thereof or to a patient not in need thereof but as a prophylactic measure. As previously stated, the use of NSAIDs as anti-prostaglandins stabilizes the endothelial barrier, thus reducing, inhibiting or preventing breakdown of endothelial cells and associated leakage. In general, the concentration of NSAID(s) in the composition ranges from about 0.1% wt to about 10% wt.

It will be understood that other bioactive ingredients can be used that are capable of inducing a desired response or treating a particular condition. These include, for example, an antifungal, anti-inflammatory, antibiotic, analgesic, immunosuppressive agent, and mixtures thereof. Suitable antibiotics include aminoglycosides, cephalosporins, macrolides, monobactrams, penicillins, quinolines, sulfonamides and tetracyclines as known in the art. Examples of immunosuppressive agents include cyclosporin, azathioprine and $Rh_9$ (D)immune globulin. These active ingredients are intended to be exemplary of suitable pharmaceutically active components.

In another embodiment, the NSAID composition may also include metalloproteinase inhibitors. Matrix metalloproteinases (MMPs) are zinc-dependent proteinase enzymes that are associated with the tumorigenic process, and/or collagenases. These enzymes are used in the angiogenic process as well as in tumor metastasis and extracellular matrix (ECM) remodeling. Inhibitors of matrix metalloproteinases may include doxycycline and naturally occurring proteins such as the family of tissue inhibitors of metalloproteinases (TIMPs), such as TIMP-1 and TIMP-2 that are involved with the inhibition of angiogenesis and are capable of inhibiting tumor growth, invasion, and metastasis which has been related to MMP inhibitory activity; TIMP-3 which is found only in the extracellular matrix; and TIMP-4 which may function in a tissue-specific fashion in extracellular matrix hemostasis; collagenase (MMP1) which degrades fibrillar interstitial collagens, gelatinase (MMP2) which mainly degrades type IV collagen, and stromelysin (MMP3) which has a wider range of action; and synthetic metalloproteinase inhibitors such as Batimastat (BB-94) and marimastat (BB-2516) which potently and specifically inhibit metalloproteinase production. These inhibitors degrade the extracellular matrix, promoting tumor invasion and metastasis, but also regulate host defense mechanisms and normal cell function. Selective inhibition is expected to inhibit reactions leading to vascularization in the inventive compositions and methods. Such matrix metalloproteinase inhibitors are also included in the invention.

In embodiments, the NSAID-containing composition contains a tetracycline class antibiotic, as an inhibitor of matrix metalloproteinase (MMP) activity, buffered to a neutral pH (around pH 7.4). For example, a 1% solution of doxycycline in water has pH of 2 to 3 due to ascorbic acid (vitamin C). While it is known that vitamin C at concentrations of 10 mg/ml inhibits corneal neovascularization, vitamin C that had been neutralized to a pH of about 7.4 retained efficacy in inhibiting corneal neovascularization. Such an anti-angiogenic effect of vitamin C has not previously been reported, nor has a possible synergistic effect between vitamin C and doxycycline, and vitamin C and NSAIDs. While not wishing to be bound by a specific theory, there may be a link between the anti-oxidant and anti-angiogenic effect of vitamin C, and the anti-inflammatory effects of NSAIDS, the effect occurring prior to VEGF activity and occurring by a non-VEGF mechanism. For topical administration, concentrations up to 30 mg/ml of a tetracycline class antibiotic may be administered, and any dose may be effective depending upon the particular patient, the underlying disease and its severity, the dosing frequency, etc., as known to one skilled in the art. The amounts of the active compounds in the composition are standard concentrations for topically applied components as known in the art.

In other embodiments, the composition includes a pharmaceutically acceptable or edible acid or a salt thereof to adjust the pH below 7.0, and generally below about pH 6.0. In other embodiments, the composition has a pH of about 5.0 or less. Suitable acids include, for example, citric acid, acetic acid, ascorbic acid, malic acid, adipic acid, fumaric acid, and mixtures thereof. In embodiments of the invention, the acid or a salt thereof, functions as a bioactive compound for certain topical applications or as a flavor for applications to areas of the oral cavity. In preferred embodiments, the acid is in the form of a citrus juice from lemons, limes, oranges, grapefruits, tangerines, tangelos, and mixtures thereof. Generally, the citrus juice is fresh squeezed juice or juice obtained from reconstituted concentrate. The most preferred citrus juice is fresh lemon juice. In further embodiments, the composition can contain a mixture of citric acid and ascorbic acid and an acid which imparts a flavor to taste.

In embodiments of the invention, the acid, which can be a citrus juice, is included in an amount to provide a solution having a pH of about 2.0-6.0, depending on the desired pH for the tissue being treated. In embodiments, the composition has a pH of about 2.0-3.0 for some topical applications to the skin and mucosa. Fresh lemon juice, for example, typically has a pH of about 2.3 to 2.4. In embodiments where the carrier is a liquid, the acid compound is included in an amount to produce a solution having a pH of about 2.0-6.0, and preferably a pH of about 2.0-5.0. In one embodiment, the composition consists essentially of citrus juice, such as lemon juice and an amount of a natural or non-nutritive sweetener to inhibit the pain and irritation normally caused by acidic solutions when applied topically.

Acidic agents are known generally to produce a burning and irritating effect when applied to sensitive tissue such as scratches or cuts on the skin, mucosa and the eye. It has been found that the anti-irritants of the invention, and particularly sodium saccharine, has an anti-irritant effect on tissue to inhibit the irritation caused by the acid added in an effective amount. Moreover, pH measurements of acid solutions containing varying amounts of sucrose and/or sodium saccharine have shown that the sucrose and sodium saccharine do not significantly alter the pH of the acidic solution. One aspect of the invention is based on the use of an anti-irritant agent without significantly adjusting the pH of the acidic solution. In addition, the vehicle containing the acid will have a substantially neutral pH, thus depending upon the acid's pK, a portion of the acid will be in the salt form.

In embodiments of the invention, the pH of the composition is adjusted as necessary to dissolve a desired active compound. For example, certain compounds are stable or soluble only in acid or alkaline solutions and cannot be easily dissolved without adjusting the pH. The anti-irritant of the invention enables the use of acidic or alkaline solutions containing compounds that are insoluble or unstable at neutral pH without irritation normally associated with acidic or alkaline solutions. In one embodiment, acid solutions having a pH of less than about 5.0 can be applied to the skin or mucosa tissue substantially without irritation.

The composition in one embodiment of the invention is an aqueous solution containing an active ingredient for applying topically to the skin, mucosa, or other tissue. Compositions for applying topically to the tissue may contain an antibiotic, antibacterial agent, analgesic or anti-inflammatory, and an anti-irritating amount of a natural or artificial sweetener. The composition is suitable for methods of treating minor cuts, blisters, wounds, scratches, and abrasions on the skin and/or mucous membranes substantially without irritation. The composition is also suitable for topical applications in the treatment of rashes, and other manifestations of allergic/atopic reactions; cold sores, shingles, and other manifestations of infection with Herpes virus. It has been found that an aqueous solution containing 25% to 35% by weight sodium saccharine and an acid, such as ascorbic, citric or acetic acid to produce a solution having a pH of about 2.5-3.0, can be applied to scratches and minor cuts on the skin substantially without irritation. The sodium saccharine is believed to provide a temporary suppression of the nerve endings on the skin to prevent or reduce the irritation. It has also found that lemon juice having a pH of about 2.5 containing about 30% by weight sodium saccharine can be applied to minor skin cuts substantially without the irritation normally associated with an acidic solution applied to a cut.

In a further embodiment, the composition is an aqueous ophthalmic preparation for treating the eyes where the preparation contains an effective amount of an anti-irritant. Generally, the ophthalmic preparation is an aqueous solution diluted to the desired concentration with a physiological saline solution containing potassium chloride, sodium chloride and glucose. In further embodiments, the ophthalmic preparation is a lactated Ringer's solution. The ophthalmic preparation can be administered in the form of drops to the eye to reduce the discomfort associated with dryness and to aid in the healing of injured conjunctiva and corneal tissue. The solution can contain a tetracycline class antibiotic at a neutral pH, a suitable buffering agent, surfactant and an anti-irritant amount of a natural or non-nutritive sweetener in addition to one or more NSAIDs.

The buffering agent is a pharmaceutically acceptable component to adjust the pH of the solution in the desired range as known to one skilled in the art. Suitable buffering agents include the combination of citric acid and a citrate. Other acids such as lactic, malic and succinic acid can be used. Phosphate salts such as monosodium dihydrogenphosphate, disodium monohydrogenphosphate, monopotassium dihydrogenphosphate, dipotassium monohydrogen-phosphate, and mixtures thereof can also be used. The surfactants can be, for example, polyoxyalkylene derivatives such as the surfactants sold under the trademarks Tween-80, Tween-60 and Tween-40. The ophthalmic composition generally is adjusted to a pH of about 6.0 to about 7.0. In further embodiments, the pH can be adjusted to below pH 6.0 without causing irritation to the tissue, or can be adjusted to a substantially neutral pH.

The ophthalmic preparation may contain about 15% to 30% by weight of a non-nutritive sweetener to serve as an anti-irritant based on the weight of the carrier. Sodium saccharine is the preferred anti-irritant for use in ophthalmic preparations. The ophthalmic preparation includes at least one NSAID in standard amounts commonly delivered to the eye by topical application. The preparation is generally applied to the eye, eyelid under surface, or ocular cavity by applying drops to the surface of the eye. The ophthalmic preparation may include other pharmaceutical agents or active compounds commonly used in ophthalmic solutions. For example, the ophthalmic solution can contain an anti-inflammatory agent, antibiotic, vasoconstrictor, antifungal, or the like, in conventional concentrations.

In a further embodiment, the composition is an irrigating solution for use in a process of irrigating a surgical site, such as an ocular cavity or in the eye to replace the vitreous humor. For example, during ocular surgery, an aqueous solution of a saccharide or disaccharide is supplied to the ocular cavity or into the eye ball to irrigate the cavity and support the eye ball during surgery. The aqueous solution can also include an anti-irritating amount of a synthetic sweetener. The surgical irrigating solution is an aqueous solution and generally contains about 15% to about 35% by weight of an artificial sweetener based on the weight of the carrier.

In a further embodiment of the invention, the composition is an oral composition effective in removing plaque and calculus deposits from the surface of teeth. Calculus deposits are generally formed of calcium phosphate and calcium carbonate that adhere to the tooth surfaces and are typically associated with inflammation and bleeding of the gums. Calculus deposits are frequently a primary cause of receding gums.

The oral composition in one embodiment of the invention is an aqueous solution containing an edible acid or salt thereof that imparts a flavor and an anti-irritant in an amount effective to inhibit pain, irritation, and inflammation to the gums. An example is the treatment of pain, inflammation and/or bleeding of gums associated with plaque and calculus deposits and/or mouth ulcers (canker sores). The oral composition can be used as a mouthwash or rinse or as a dentifrice in combination with brushing or other mechanical cleaning of the teeth. The edible acids that impart a flavor include acids in the form of a citrus juice, generally including, for example, citric acid, ascorbic acid, acetic acid, tartaric acid, malic acid, fumaric acid, and mixtures thereof. The acid is included in an amount to provide a pH of less than 7.0, and generally about 2.0 to 6.0, and preferably about pH 5.5 to 6.0. In a preferred embodiment, the oral composition is fresh lemon juice. In an embodiment, the oral composition has a pH of about 3.0-4.0. In further embodiments, the oral composition contains a mixture of citric acid and ascorbic acid in amounts to provide a pH of about 6.0 or less, and generally about pH 5.5 to pH 6.0.

The anti-irritant in the oral composition is preferably an artificial or natural sweetener. The preferred anti-irritant is sodium saccharine, aspartame or cyclamates, in the concentration of about 15% to 30% by weight. Alternatively, the anti-irritant can be sorbitol, mannitol, xylitol, and maltitol or mixtures thereof. The composition further contains a mixture of an artificial sweetener and a natural sweetener. Generally, the disaccharide are less preferred for oral rinses to minimize the plaque formation. In further embodiments, the oral composition can contain a flavoring agent, a fluoride source, anti-carrier agent, antibacterial agent, humectant, emulsifier, bleaching agent, surfactant or solubilizing agent. Although the oral composition is preferably an aqueous solution, the solution can contain up to 20% by weight of a cosolvent, such as ethyl alcohol.

Suitable flavoring agents include natural or synthetic flavors or oils. These flavors include citrus oils, such as lemon oil, lime oil, grapefruit oil, fruit essences, peppermint oil, spearmint oil, clove oil, bay oil, eucalyptus oil, cinnamon oil, wintergreen oil, as well as other flavorants such as bubble gum, grape, cherry and others known to one skilled in the art.

In embodiments of the invention, the oral composition is preferably an aqueous composition applied to the tooth surface either alone or in combination with mechanical application. In one embodiment of the invention, the oral composition contains fresh lemon juice and sodium saccharine having a pH of about 2.0 to 4.0. This oral composition is applied to the calculus deposits with a soft dental brush or proxy brush to brush the composition onto the calculus deposits and between the teeth for a sufficient amount of time to remove or loosen the calculus deposits. Generally, the oral composition is applied followed by neutralizing the acid in the mouth and on the tooth surface. Neutralizing the acids can be by rinsing with water or other mouth rinse to wash and remove the acid from the tooth surfaces. Alternatively, a commercially available dentifrice, such as tooth paste, can be used by brushing to neutralize and remove the acid from the tooth surfaces.

Typically, the oral composition at a pH of about 2.0-4.0 effectively removes or loosens the calculus deposits without the need for mechanical abrasion or cleaning. The composition for applying directly to the tooth surfaces can include a pH adjusting agent or buffer to raise the pH to at least 5.0, and alternatively to at least pH 5.5, to reduce the effects of the acid on the enamel and dentin surfaces of the tooth.

Regular cleaning of the tooth surfaces with the oral composition has shown to remove substantial amounts of calculus deposits on the teeth and to loosen the deposits. In some instances, the calculus deposits are completely removed. In other instances, the deposits are loosened so that they can be easily removed by a dentist or hygienist during routine cleaning by mechanical action. The composition is also found to be effective in preventing or reducing the amount of the calculus deposits which normally form on the teeth. A suitable oral composition is an aqueous solution containing an edible acid in a concentration to provide a pH of about 2.0 to 6.0, generally about pH 5.5 to pH 6.0, and about 20% to about 30% by weight of an anti-irritant, such as sodium saccharine.

In a further embodiment, the oral composition can contain a physiologically acceptable alkaline agent to form a substantially neutral pH solution or a solution having a pH 7.0 or greater. Examples of suitable alkaline agents include carbonates and bicarbonates such as sodium bicarbonate. Compositions containing sodium bicarbonate can be used as an oral rinse or an aid during the brushing of the teeth. In preferred embodiments, the oral composition contains an artificial sweetener in an effective amount to avoid or reduce irritation to the mouth, teeth and gums.

In another embodiment, the carrier is a solid and the composition is in a tablet or lollipop form that can be placed in the mouth to dissolve for treating the mouth, teeth and gums. For example, a tablet can be produced from a water soluble carrier containing a mixture of an acidic agent for treating of the teeth and gums, or one or more NSAID and one or more of the components previously describe such as an effective amount of an anti-irritant. Alternatively, a tablet can be formed containing an NSAID such as aspirin, and an anti-irritant where the tablet can be chewed or swallowed. The anti-irritant reduces the irritation to the stomach normally experienced by aspirin and other bioactive compounds. In further embodiments the composition includes a water soluble carrier, an alkaline agent and an anti-irritant.

In embodiments of the invention, the carrier is solid or semi-solid at room temperature that is able to release the active component(s) and anti-irritant to the delivery area. In embodiments of the invention, suitable solid carriers included sucrose, corn syrup solids, and other confectionery compositions. In embodiments, the carrier is a lozenge, hard candy, lollipop or gel and the like comprising a mixture of a natural sweetener and an artificial sweetener such as sodium saccharine and at least one active component. Preferably, the solid carrier is water soluble that can dissolve in the mouth to release the active agent and anti-irritant. Preferred natural sweeteners include sorbitol, mannitol and xylitol.

Examples of semi-solid carriers include gels, chewing gums and other chewable compositions and compositions as known in the art. The carrier can be a conventional toothpaste or dentifrice gel. In one embodiment of the invention, the composition is in the form of a chewing gum comprising a chewing gum base, an active component and a sweetener in an amount to provide an anti-irritant effect. The active component can be an NSAID analgesic, such as aspirin, acetaminophen or ibuprofen, and the anti-irritant can be an artificial sweetener, such as sodium saccharine. Oral compositions preferably contain an effective amount of a fluoride to treat the tooth surfaces.

The chewing gum base of the invention can be a conventional gum base as known in art that can contain one or more solvents, plasticizer, flavorants and colorants. The composition generally contains up to about 50% by weight of a gum base based on the total weight of the composition. Suitable chewing gum bases include natural and synthetic elastomers and rubbers. Natural chewing gum bases include natural rubber, chickle, jeluting, gutta percha and croun gum. Other gum bases includes rosins, such as comatone resin, pontianak resin, copel gum, kauri gum, dammar gum, sweet bay gum, spruce gum, and balsams. Synthetic elastomers includes butadiene-styrene copolymers, isobutylene-isoprene copolymers, polyethylene, polyisobutylene, polyvinylacetate and copolymers of vinyl acetate.

In embodiments of the invention, the chewing gum includes an edible acid and an effective amount of a sweetener as an anti-irritant to inhibit irritation of the gums caused by the acid. The acid is combined with the chewing gum base in an amount to adjust the pH in the mount to about pH 2.0 to pH 6.0, and preferably about pH 2.0 to pH 5.0. The anti-irritant are combined with the chewing gum base in an effective amount to mask the sour taste of the acid and to provide an anti-irritant effect. Generally, the anti-irritant is an artificial sweetener included in a concentration of about 10% to 20% by weight based on the weight of the gum base and about 10% to about 30% based on the total weight of gum composition.

In a further embodiment of the invention, the composition includes a water soluble base, acidic component, bioactive agent and an anti-irritant in an effective amount to inhibit irritation caused by the acidic component and the bioactive agent. Typically, the composition is a tablet that can dissolve quickly in water. One example of soluble tablets contains sodium bicarbonate, citric acid, an NSAID analgesic such as aspirin, and saccharine. The composition can also include a stabilizing agent.

In one embodiment of the invention, the acid is ascorbic acid (Vitamin C). Ascorbic acid is desirable in some instances because it is naturally occurring and bio-compatible. Ascorbic acid also has several beneficial properties when applied topically and taken orally as a source of Vitamin C. A disadvantage of ascorbic acid is that it is unstable in the presence of oxygen. Ascorbic acid is known to rapidly decompose in the presence of oxygen to form L-ascorbic acid 2-hydrogen sulfate, which then converts to dehydroascorbic acid. Glutathione, which is present in the body and cells, helps to reverse the L-ascorbic acid-dehydroascorbic acid reaction to maintain the ascorbate in the body tissues.

Liquid and solid compositions of the invention can be prepared containing ascorbic acid either alone as the sole acidifying agent or in combination with other acids. In one embodiment of the invention, the composition contains ascorbic acid as an acidic component in combination with an ascorbic acid stabilizing agent. The stabilizing agent is included in an amount sufficient to provide a stabilized ascorbic acid composition and to inhibit or prevent the oxidation and degradation of the ascorbic acid. The actual amount of the stabilizing agent provided can depend on the composition, the concentration of the ascorbic acid, and particular stabilizing agent being used. In one embodiment, combinations of different stabilizing agents can be used so long as the stabilizing agents are compatible.

A number of suitable stabilizing agents for ascorbic acid can be used either alone or in combination. Examples of suitable stabilizing agents include known antioxidants and free radical scavenging agents. In one embodiment, the stabilizing agent is an alkali metal sulfite or bisulfite such as sodium sulfite and potassium sulfite. Mannitol is one example of a suitable free radical scavenging agent that can be used as a stabilizing agent. Other suitable stabilizing agents include a magnesium ion source such as magnesium sulfate, and other magnesium salts, phosphoric acid derivatives and metabisulfite derivatives. Suitable phosphonic acid derivatives include methylenediamine tetra(methylenephosphonic acid), hexamethylenediamine tetra(methylenephosphonic acid), diethylenetriamine tetra(methylenephosphonic acid), and salts thereof, and particularly sodium salts thereof. Other stabilizing agents for ascorbic acid include naturally occurring agents such as cysteine and various plant extracts and derivatives. Examples of natural stabilizers includes proanthocyanidins from pine bark or grape seeds, catechins, xanthines and flavonoids from Japanese green tea leaves, rose hips and acerola. Botanical extracts and herbal preparations can also be obtained from eucalyptus oil, gingko biloba, *Echinacea,* and *Enblica officinalis.*

Ascorbic acid is relatively stable as a solid in the absence of moisture and air. Aqueous solutions of ascorbic acid in air can cause rapid degradation of ascorbic acid. The shelf life of liquid compositions, and particularly aqueous compositions, can be extended by including an effective amount of a stabilizing agent. The amount of the stabilizing agent can vary depending on the stabilizing agent used. Typically, the stabilizing agents are used in concentrations of about 0.5 wt % to about 5.0 wt % based on the weight of the ascorbic acid.

Liquid compositions can also contain organic liquids, cosolvents or dispersing agents in an amount to stabilize the ascorbic acid. Examples of suitable organic liquids include silicone oils, propylene glycol and butylene glycol with suitable emulsifiers to form a stable emulsion.

In one embodiment, the composition is an aqueous composition containing about 0.1 g/ml to about 0.3 g/ml ascorbic acid, about 0.1 g/ml to about 0.3 g/ml of non-nutritive sweetener as an anti-irritant and stabilizing agent to inhibit the degradation of the ascorbic acid. The composition can also contain a second acid or buffering agent to maintain the pH in the desired range. The pH is generally less than pH 6.0, and may be about pH 5.0 or less. In one embodiment, the composition has about pH 4.0 or less. An example of a suitable stabilizing agent is magnesium sulfate in a concentration of about 0.02 g/ml to about 0.04 g/ml. The composition can also contain a bioactive agent such as an anti-inflammatory agent or analgesic agent.

The following non-limiting examples of the invention demonstrate various embodiments of the invention.

EXAMPLE 1

This example demonstrates that sodium saccharine and sucrose have little effect on the pH of an aqueous composition of the invention. In this example, samples 1-6 were prepared from fresh lemon juice which was filtered to remove the pulp and other solid materials. Sample 1 was plain lemon juice with no sweeteners or additives. Samples 2-4 contained 3.0 ml lemon juice and sodium saccharine obtained under the trademark Sweet-N-Low in the amounts indicated in Table 1. Sample 5 contained 3.0 ml lemon juice and sucrose obtained as table sugar. Sample 6 was obtained by combining Samples 4 and 5 together. The proportions of the components and the resulting pH are indicated in Table 1 below.

TABLE 1

| Sample No. | Vol. of Lemon Juice | Anti-Irritant | pH |
|---|---|---|---|
| 1 | 3.0 ml | None | 2.36 |
| 2 | 3.0 ml | 1.0699 g saccharine | 2.25 |
| 3 | 3.0 ml | 1.9066 g saccharine | 2.23 |
| 4 | 3.0 ml | 2.888 g saccharine | 2.35 |
| 5 | 3.0 ml | 3.3254 g sugar | 2.17 |
| 6 | 3.0 ml | 3.3254 g sugar 2.888 g saccharine | 2.24 |

The data demonstrate that the addition of saccharine and sucrose to lemon juice does not significantly change the pH. The pH of each sample was measured at 25° C. from two to six times to obtain a constant measurement. The pH meter was calibrated the measurement of each sample. The saccharine of samples 4 and 6 did not completely dissolve and were presumed to be saturated solutions.

EXAMPLE 2

An oral composition was prepared from 3.0 ml of fresh lemon juice and 1.0 gram of non-nutritive sweetener containing saccharine obtained under the trademark Sweet-N-Low. An adult male subject having calculus deposits on the subgingival and supragingival tooth surfaces applied the composition once every two days using a small proxy brush for inserting between the teeth followed by rinsing with the oral composition. The patient reported to irritation, burning or discomfort to the gum surfaces or to the teeth normally associated with an acidic solution when applied to the gums and tooth surfaces. After two weeks, significant reduction in the calculus depositions on the teeth were observed and the remaining calculus deposits easily separated from the tooth surface by the use of a dental tool.

EXAMPLE 3

A topical composition was prepared from about 3.0 ml fresh lemon juice and 1.0 g of a sweetener containing sodium saccharine obtained under the trademark Sweet-N-Low. The resulting solution was applied to a scratch on the skin of an adult male patient. The patient reported substantially no irritation or burning of the scratch.

EXAMPLE 4

The composition of Example 3 was applied to the surface of the eye of an adult male patient. The patient reported no burning or irritation in the eye.

EXAMPLE 5

A composition can be prepared from a chewing gum base, ascorbic acid as an active component, and sodium saccharine as an anti-irritant. The composition contains about 5.0% by weight ascorbic acid and about 10.0% by weight sodium saccharine based on the weight of the composition. The composition is administered by chewing to disperse the ascorbic acid and sodium saccharine to the surfaces of the patient's teeth for sufficient to treat the tooth surfaces. The ascorbic acid and the chewing action assist in removing calculus deposits from the tooth surfaces while the sodium saccharine provides an anti-irritant effect on the tooth and gum surfaces.

EXAMPLE 6

A composition is prepared from a sorbitol base to form a hard candy. The composition contains about 5.0% citric acid, acetic acid, ascorbic acid and mixtures thereof in an amount to adjust the pH of the saliva to about pH 4.0 to 6.0 when placed in the mouth. The composition also contains about 10.0% by weight sodium saccharine based on the weight of the composition to inhibit irritation to the tooth and gum surfaces. The composition is administered by placing in the mouth to dissolve the carrier and disperse the acid and anti-irritant. The carrier dissolves at a rate to provide a sustained release of the active component and anti-irritant.

EXAMPLE 7

A tablet is prepared from sorbitol as a carrier material, aspirin and about 10% by weight sodium saccharine. The tablet is administered orally and is swallowed whole by the patient to administer the aspirin to the patient. The patient experiences less stomach irritation than that experienced by patients when the anti-irritant is not used.

One embodiment of the invention is a method using pH neutralized ascorbic acid effective for reducing neovascularization. pH neutralized ascorbic acid may be used in any concentration, amount, formulation etc. that would be used with non-neutralized ascorbic acid to achieve the same effect (e.g., antioxidant, anti-neovascular, etc.). In various embodiments it may be topically applied to a mucous membrane such as the mouth or nose, to intact or compromised skin, or to the eye, or injected into the eye (e.g., subconjunctival injection, intravitreal injection, etc.) or other sites, or instilled in a body cavity (e.g., in a bladder following tumor biopsy, removal, etc.). The pH neutralized ascorbic acid retains efficacy in reducing neovascularization over a range of concentrations with no significant difference when compared to non-pH neutralized ascorbic. However, ascorbic acid neutralized to a pH of about 7 is less irritating to the surface it contacts than non-neutralized ascorbic acid, which is about pH 2.5. A pH neutralized ascorbic acid composition will be better tolerated with respect to patient comfort when it is injected, topically applied, instilled, etc. and cause less irritation to the tissue.

Ocular neovascularization is the pathologic ingrowth of blood vessels in the eye, for example, in the cornea (a normally transparent avascular tissue), retina, or choroid. The new vessels can cause reduced vision or loss of vision due to bleeding and subsequent scarring, fibrosis, etc.

Blood vessel growth or formation can be due to diverse events. These include hypoxia (e.g., in diabetes), inflammatory responses (e.g., blepharitis), microbial infection (e.g., keratitis), physical insult (e.g., improper use of contact lenses, surgery including corneal surgery (e.g.,LASIK® surgery, photorefractive keratectomy (PRK), or other corneal procedures), chemical insult (e.g., toxins), pharmacologic agents, or other factors (e.g., graft rejection). More specifically, an inflammatory response may follow corneal transplant. Ocular microbial infections include but are not limited to trachoma, viral interstitial keratitis, and keratoconjunctivitis. Corneal insult may be due to contact with acidic or alkaline solutions, trauma, improper hygiene and/or compliance with contact lens use, such as extended wear lenses, or chemical agents such as silver nitrate. Other factors leading to ocular neovascularization include mechanical irritation of the limbal sulcus, corneal hypoxia, epithelial cell erosion or hypertrophy. In dry eye disease (conjunctiva sicca), the dehydrated conditions cause sloughing off of the epithelium, resulting in new vessel formation. In the cornea, these insults can lead to invasion of capillaries from the limbal plexus, resulting in neovascularization.

Corneal neovascularization is a major cause of ocular morbidity. Approximately 4% of the patients in a general ophthalmic practice were affected, according to one estimate. In many cases, corneal neovascularization is associated with decreased visual acuity secondary to stromal edema, lipidic deposits, causal keratitis, and scarring.

The cornea contains both angiogenic factors such as vascular endothelial growth factor (VEGF) and anti-angiogenic factors. Angiogenesis occurs when the balance is shifted to favor or up-regulate angiogenic factors and/or to down regulate anti-angiogenic factors.

Methods of treating ocular neovascularization have included treatment of the underlying condition, topical corticosteroid application for gross and active vascularization, diathermy of large feeding vessels and corneal laser photocoagulation for treatment of superficial vascularizations with infiltration of granulation tissue (pannus), and limbal grafting for severe chemical injuries and limbal epithelium loss. Long term use of topical corticosteroids is associated with ocular hypertension and cataract progression.

One embodiment of the method comprises administration or application of various concentrations of ascorbic acid that have been neutralized. That is, ascorbic acid with a pH of about 2.5 is treated with a base, such as sodium hydroxide or other base as known to one skilled in the art, to adjust the composition to a substantially neutral pH of about 7. Various concentrations of neutralized ascorbic acid are effective in reducing ocular neovascularization, and lack the irritant effects of a pH 2.5 ascorbic acid solution.

The neutralized ascorbic acid ocular treatment method limits, reduces, slows the rate of, or prevents ocular neovascularization and/or causes regression of existing new blood vessels. This is generally referred to as reduced neovascularization, although the term encompasses any degree of inhibition by any method and also encompasses any degree of regression of existing vessels. In various embodiments, doses and formulations of neutralized ascorbic acid are administered to a patient in addition to, or as treatments for, an ocular pathology. The pathology may include, but is not limited to, diabetic retinopathy, age-related macular degeneration, uveitis, ischemic retinopathies, iritis, iritis rubeosis, retinitis of prematurity, cyclitis, sickle cell retinopathy; or as a postoperative treatment, e.g. after corneal transplant or ocular surgery including corneal surgery (e.g.,LASIK® surgery, photorefractive keratectomy (PRK), or other corneal procedures. The inventive methods and compositions may desirably inhibit ocular and non-ocular neovascularization that occurs from any event, for example, due to disease, hypoxia, trauma, physical or chemical insult, etc.

Ocular neovascularizations may be superficial or deep and may lead to loss of optical transparency through stromal hemorrhage, scarring, lipid deposition, etc. Neovascularizations may occur in any area of the eye, such as the cornea, retina, conjunctiva, or choroid. The presence of new vessels may result in an increased intraocular pressure, termed neovascular glaucoma or ocular hypertension. The new vessels may lead to hemorrhage and fibrosis, and result in structural damage to the eye with subsequent decreased visual acuity. For example, corneal burns result in the formation of new vessels that can decrease vision as they infiltrate and penetrate the cornea. In corneal transplants, new blood vessels from the limbus penetrate the cornea and may result in rejection of the engrafted tissues. Thus, control or prevention of new vessels to any extent is desirable.

In another embodiment the inventive composition or formulation comprises a pharmaceutically acceptable formulation (that is, containing buffers, excipients, etc., known to one skilled in the art) of neutralized ascorbic acid that is administered to an ocular area topically (such as eye drop solution), or by injection (such as subconjunctival, intravitreal, retrobulbar, etc.), or by other methods to limit, reduce, slow the rate of, or prevent ocular neovascularization. The composition is adjusted with base to a pH of about 7.

The concentration of ascorbic acid in the pH neutralized composition is from about 250 µg/ml to about 200 mg/ml. In another embodiment, the ascorbic acid concentration is about 10 mg/ml to about 100 mg/ml. While concentrations of ascorbic acid ranging between about 250 µg/ml up to about 100 mg/ml are useful for reducing neovascularization, it will be appreciated that lower concentrations up to 250 µg/ml (e.g., 50 µg/ml, 100 µg/ml, 200 µg/ml, etc.) may also be useful for anti-oxidant and other effects, and are a part of the invention.

The formulation is administered to an ocular area topically, such as eye drop solutions, ointments, gels, creams, salves, etc., or by injection such as subconjunctival, intravitreal, retrobulbar, etc. The composition may be in a slow release formulation, may be contained in microspheres, microcapsules, liposomes, etc. as known to one skilled in the art.

The formulation may also contain other agents, including but not limited to one or more of an NSAID, antiproliferative agent, metalloproteinase inhibitor, antibiotic, and/or other antioxidants. The NSAID and metalloproteinase inhibitor may provide a synergistic effect as previously described. The composition may also contain an antibiotic such as that in the tetracycline class also as previously described. Such agents are known to one skilled in the art.

This embodiment of the invention will be further appreciated with respect to the following examples.

EXAMPLE 8

Thirty-six eyes belonging to thirty-six male Long Evans pigmented rats (200 g to 250 g) were divided into three groups. Treated eyes were topically administered solutions of saline or ascorbic acid, as subsequently described. Artificial corneal burns were induced. All the eyes were examined to exclude any eyes with corneal scars and/or neovascularizations prior to induction. More specifically, topical administration of the described agents was administered twice a day to rats in which corneal burns had been artificially induced by application of silver nitrate (70%) and potassium nitrate (30%).

Neovascularization was induced in all eyes using silver nitrate cauterization. The animals were first anesthetized by intraperitoneal injection of a mixture of ketamine hydrochloride (25 mg/kg) with xylazine hydrochloride (5 mg/kg). The cornea was then anesthetized by a drop of 0.5% proparacaine hydrochloride and allowed to dry. One cornea of each animal was cauterized by pressing an applicator stick (diameter of 1.8 mm) coated with 75% silver nitrate/25% potassium nitrate (Arzol Chemical Co., Keen, N.H.) to the central cornea for ten seconds (using a stopwatch) under the operating microscope. Excess silver nitrate was removed by rinsing the eyes with 5 ml balanced salt solution. To increase the reproducibility of the injuries, one investigator cauterized all animals. Following cauterization, the animals were randomly divided into six groups to eliminate any potential bias in the degree of burns within the different groups. Two drops of each drug were applied topically to each cornea immediately following cauterization; treatments were administered two times per day for seven days.

Group 1 (number of animals (n)=8) received 100 mg/ml pH non-neutralized ascorbic acid. All remaining experimental groups received ascorbic acid neutralized to about pH 7 as previously described in the following concentrations: Group 2 (n=8) received 100 mg/ml (10%$^{w/v}$) neutralized ascorbic acid; Group 3 (n=8) received 50 mg/ml (5%$^{w/v}$) neutralized ascorbic acid; Group 4 (n=8) received 10 mg/ml (1%$^{w/v}$) neutralized ascorbic acid; Group 5 (n=8) received 5 mg/ml neutralized ascorbic acid (0.5%$^{w/v}$); Group 6 (n=8) received 1 mg/ml neutralized ascorbic acid (0.1%$^{w/v}$); Group 7 (n=8) received 500 µg/ml neutralized ascorbic acid (0.05%$^{w/v}$); Group 8 (n=8) received 250 µg/ml neutralized ascorbic acid (0.025%$^{w/v}$). Group 9 (n=8) received two drops of saline and served as the control. All concentrations of ascorbic acid were titrated with saline.

The presence of new vessels (neovascularization) and the extent of new vessel formation was assessed by slit lamp photography and in some embodiments, by histology. Inhibition of vessel proliferation was evaluated by measuring vessel progression from the outer cornea (corneal limbus) into the cornea. As previously described, it will be appreciated that any reduction of new vessel proliferation and/or regression of existing vessels is therapeutic, and that complete inhibition and/or regression is not required, and also that reduction includes regression of existing vessels.

All animals were anesthetized as described above and their corneas evaluated by slit-lamp microscopy on the third and sixth days. Corneal photographs were taken with ×25 magnification using a camera attached to the slit-lamp microscope (Topcon SL-7E, Tokyo Japan) on the seventh day. Neovascularization was evaluated by an examiner who was blinded as to the treatment groups to minimize the observer bias.

Corneal neovascularization was assessed by scanning (Cano scan 9900F, Canon, Tokyo Japan) the slit lamp photographs into high resolution digital images. The corneal surface covered with neovascular vessels was measured on the photographs as the percentage of the total area of the cornea. The percentage area of corneal neovascularization was determined by outlining the areas with corneal vessels and comparing these to the total corneal surface using image j software (Wayne Rasband at the Research Services Branch,-National Institute of Mental Health, Bethesda Md.). The area of neovascularization was measured in terms of pixels and its ratio to the entire corneal area was determined as the percentage of corneal neovascularization. The extent of the scar was also evaluated by calculating the percentage of the corneal surface that was covered by the scar. A drawing of corneal blood vessels was made to compare with digital photos and ensure that no vascular area was omitted during calculation of percent area.

For each eye, the extent of burn stimulus response was scored as 0 (no blister, not raised above corneal surface), +1 (small blister, raised slightly above the surface), +2 (medium blister, raised moderately above the surface), or +3 (large blister). Only corneas with a burn stimulus score of +2 or higher were included for the calculation of the mean burn stimulus and neovascularization scores in each group.

Percent inhibition was calculated by comparing the mean percentage of neovascularization in each treated group to that in the control group. After scoring the burn stimulus and the percentage of neovascularization for all groups, the animals were sacrificed on the seventh day.

Statistical analyses were performed using each animal as an experimental unit with Statistical Analysis System (SPSS 11.5) software. Kruscal-Vallis and Mann-Whitney U Analysis was conducted and treatment means were separated at $p<0.05$ with least significant difference (LSD) test. A $\rho$ value<0.05 was considered significant.

For embodiments with histopathologic evaluation, sedated animals were euthanized with inhaled $CO_2$ and enucleation was performed immediately. The globes were penetrated with a 27-gauge needle, 1.0 mm from the limbus at the 3 and 9 o'clock meridians to allow the fixative to fill the eyes rapidly. The eyes were prepared for histologic examination using 10% formaldehyde. After fixation for twenty-four hours, the eyes were removed from the fixative and corneas were dehydrated and sectioned. The corneas were then soaked in xylene and paraffin, and later embedded in paraffin and cut at 1 μm for staining with hematoxylin and eosin (H&E) for light microscopy.

Light microscopic examination was performed on every microscopic section. Sections were examined by dividing the corneas into two halves through the center of the lesion and were evaluated with regard to the intensity of new vessels, polymorphonuclear (PMN) leucocytes, edema, and fibroblastic activity.

The mean ±standard deviation burn stimulus scores and the mean ±standard deviation percent of neovascularization relative to total corneal area of each cornea in the treatment and control groups are shown in Table 1.

TABLE 1

Degree of Corneal Neovascularization

| Ascorbic Acid 100 mg Non pH Neutralized | | | Ascorbic Acid 100 mg pH Neutralized | | |
|---|---|---|---|---|---|
| Subject | OD | OS | Subject | OD | OS |
| 1 | 20% | 22% | 1 | 15% | 3% |
| 2 | 0% | 0% | 2 | 28% | 0% |
| 3 | 10% | 33% | 3 | 0% | 54% |
| 4 | 25% | 30% | 4 | 31% | 5% |
| AVE = 17.5 ± 12.8% (n = 8) | | | AVE = 17.0 ± 19.3% (n = 8) | | |

| Ascorbic Acid 50 mg pH Neutralized | | | Ascorbic Acid 10 mg pH Neutralized | | |
|---|---|---|---|---|---|
| Subject | OD | OS | Subject | OD | OS |
| 1 | 10% | 5% | 1 | 0% | 0% |
| 2 | 15% | 35% | 2 | 31% | 27% |
| 3 | 32% | 22% | 3 | 20% | 15% |
| 4 | 3% | 0% | 4 | 22% | 26% |
| mean = 15.2 ± 13.3% (n = 8) | | | mean = 17.6 ± 11.9% (n = 8) | | |

| Ascorbic Acid 5 mg pH Neutralized | | | Ascorbic Acid 1 mg pH Neutralized | | |
|---|---|---|---|---|---|
| Subject | OD | OS | Subject | OD | OS |
| 1 | 20% | 60% | 1 | 49% | 47% |
| 2 | 35% | 26% | 2 | 15% | 27% |
| 3 | 0% | 30% | 3 | 48% | 29% |
| 4 | 60% | 0% | 4 | 5% | 17% |
| mean = 28.9 ± 23.1% (n = 8) | | | mean = 29.6 ± 16.9% | | |

| Ascorbic Acid 500 μg pH Neutralized | | | Saline Control | | |
|---|---|---|---|---|---|
| Subject | OD | OS | Subject | OD | OS |
| 1 | 54% | 50% | 1 | 65% | 64% |
| 2 | 69% | 63% | 2 | 70% | 75% |
| 3 | 70% | 66% | 3 | 68% | 63% |
| 4 | 61% | 48% | 4 | 71% | 70% |
| mean = 60.1 ± 8.5% (n = 8) | | | mean = 68.3 ± 4.1% (n = 8) | | |

| Ascorbic Acid 250 μg pH Neutralized | | |
|---|---|---|
| Subject | OD | OS |
| 1 | 68% | 65% |
| 2 | 69% | 63% |
| 3 | 70% | 66% |
| 4 | 61% | 48% |

Neutralized ascorbic acid solutions at concentrations ranging from 100 mg/ml to 500 μg/ml significantly inhibited corneal neovascularization.

At 100 mg/ml, the mean inhibition was 82.5% (17.5% vascularization) for eyes treated with non-neutralized ascorbic acid solution (p=0.001 compared to control), while the mean inhibition was 83.0% (17.0% vascularization) for eyes treated with pH neutralized ascorbic acid solution (p=0.001 compared to control). All concentrations of neutralized ascorbic acid solutions (50 mg/ml, 10 mg/ml, 5 mg/ml, 1 mg/ml) resulted in significant inhibition compared to control eyes (p=0.001). At 500 µg/ml ascorbic acid, the mean inhibition was 39.9% (60.1% vascularization), while mean inhibition in control eyes was 31.7% (68.3% vascularization) (p=0.04). At 250 µg/ml ascorbic acid, the differences were not significant (p=0.185)

Figure 1E:
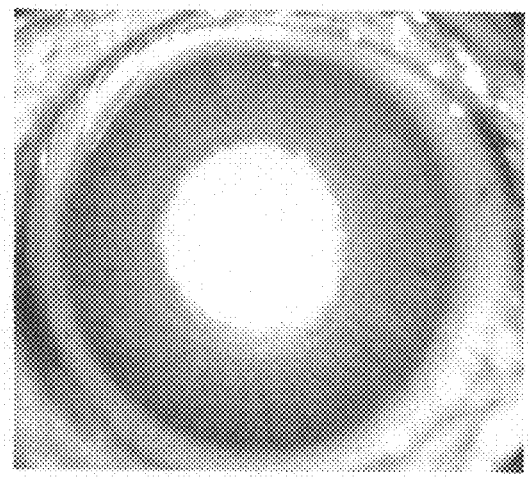
Figure 2:
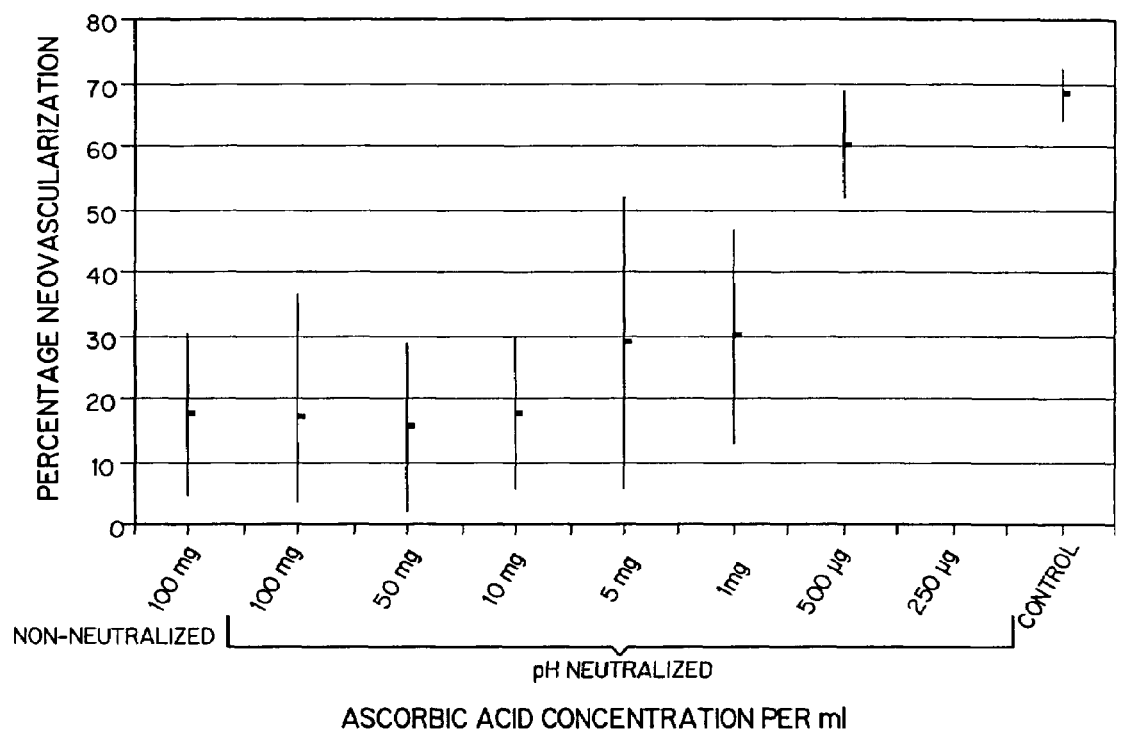
FIG. 2 shows results from one embodiment of the invention.

FIG. 1 shows photographs of eyes in which corneal neovascularization has been induced by the method previously described, and treated, respectively, with saline (FIG. 1A, control), 500 µg/ml pH neutralized ascorbic acid (FIG. 1B), 1 mg/ml pH neutralized ascorbic acid (FIG. 1C), 100 mg/ml pH neutralized ascorbic acid (FIG. 1D), and 250 µg/ml pH neutralized ascorbic acid (FIG. 1E). Results are shown graphically in FIG. 2. Treatment with 100 mg/ml ascorbic acid non-pH neutralized resulted in about 81% inhibition of neovascularization (about 19% neovascularization). Treatment with 100 mg/ml ascorbic acid pH neutralized resulted in about 82% inhibition of neovascularization (about 18% neovascularization). Treatment with 50 mg/ml ascorbic acid pH neutralized resulted in about 83.5% inhibition of neovascularization (about 16.5% neovascularization). Treatment with 10 mg/ml ascorbic acid pH neutralized resulted in about 81% inhibition of neovascularization (about 19% neovascularization). Treatment with 5 mg/mi ascorbic acid pH neutralized resulted in about 70% inhibition (about 30% neovascularization). Treatment with 1 mg/ml ascorbic acid pH neutralized resulted in about 69% inhibition (about 31% neovascularization). Treatment with 500 µg/ml ascorbic acid pH neutralized resulted in about 40% inhibition (about 60% neovascularization). Treatment with 250 µg/ml ascorbic acid pH neutralized resulted in about 33% inhibition (about 67% neovascularization). Treatment with saline (control) resulted in about 31% inhibition (about 69% neovascularization).

EXAMPLE 9

The effect of pH neutralized and non-neutralized ascorbic acid administered topically to eyes at various concentrations was determined. Rats were subject to induced corneal neovascularization as previously described and administered pH neutralized and non-neutralized ascorbic acid and saline (control) at the same concentrations as previously described. An electroretinogram (ERG) was performed to evaluate the eye's electrical responses to a flash of light using an electrode placed on the surface of the eye (e.g., cornea) as known to one skilled in the art.

A concentration 100 mg/ml of non-pH neutralized ascorbic acid resulted in two eyes showing a 60% decrease and a 70% decrease, respectively, in ERG. There was also partial retinal detachment. A concentration of 100 mg/ml of pH neutralized ascorbic acid resulted in two eyes showing a 100% decrease in ERG (flat ERG). The eyes showed neither cataracts nor retinal detachment. After intravitreal injection there was vitreous haze and retinal edema. A concentration of either 10 mg/ml or 1 mg/ml, of either pH neutralized ascorbic acid or non-pH neutralized ascorbic acid, resulted in no significant decrease in ERG (n=6 for each group).

While various embodiments have been chosen to illustrate the invention, it will be understood by those skilled in the art that various modifications can be made without departing from the spirit and scope of the invention as defined in the following claims. For example, pH neutralized ascorbic acid for reducing neovascularization, reducing inflammation, providing an anti-oxidant effect, etc. may be applied to cells in culture and in other in vitro and ex vivo application to reduce irritation. Other embodiments are also contemplated.

What is claimed is:

1. A method of reducing neovascularization comprising administering to an individual a composition comprising an effective concentration from about 250 µg/ml to about 100 mg/ml of ascorbic acid in a composition neutralized to a pH of about 7 under conditions sufficient to reduce neovascularization wherein the composition further comprises at least one of an anti-irritant sweetener, a non-steroidal anti-inflammatory drug (NSAID), or a steroid, and wherein if topically administered the composition further comprises an NSAID.

2. The method of claim 1 wherein the concentration of ascorbic acid in the composition ranges from about 500 µg/ml up to about 100 mg/ml.

3. The method of claim 1 wherein the composition is administered topically, by injection, or by instillation in a body cavity.

4. The method of claim 1 wherein the composition is administered to at least one of skin, eye, or a mucous membrane.

5. The method of claim 1 where the individual has at least one of diabetic retinopathy, age-related macular degeneration, uveitis, ischemic retinopathies, iritis, iritis, rubeosis, retinitis of prematurity, cyclitis, sickle cell retinopathy, corneal transplantation, ocular surgery, hypoxia, trauma, physical insult, or chemical inside.

6. The method of claim 1 wherein the composition further comprises a metalloproteinase inhibitor, a non-steroidal anti-inflammatory drug, an antibiotic, an antiproliferative drug, or combinations thereof.

7. The method of claim 1 wherein the composition further includes at least one non-steroidal anti-inflammatory drug and at least one metalloproteinase inhibitor to provide a synergistic effect in reducing ocular neovascularization.

8. A method of reducing ocular neovascularization comprising administering to an individual a composition comprising an effective concentration of ascorbic acid from about 250 µg/ml to about 100 mg/ml ascorbic acid adjusted to a pH of about 7 in a biocompatible composition under conditions sufficient to reduce ocular neovascularization wherein the composition further comprises an anti-irritant sweetener, a non-steroidal anti-inflammatory drug (NSAID), or a steroid, and wherein a topically administered composition contains an NSAID.

9. The method of claim 1 wherein the sweetener is a natural sweetener or non-nutritive sweetener.

10. The method of claim 8 wherein the sweetener is a natural sweetener or non-nutritive sweetener.

* * * * *